United States Patent [19]

Darnell

[11] Patent Number: 4,473,073
[45] Date of Patent: Sep. 25, 1984

[54] MYRINGOTOMY TUBE INSERTER AND METHOD FOR INSERTING MYRINGOTOMY TUBES

[75] Inventor: W. Dale Darnell, Caledonia, Miss.

[73] Assignee: Microtek Medical Incorporated, Columbus, Miss.

[21] Appl. No.: 340,939

[22] Filed: Jan. 20, 1982

[51] Int. Cl.³ .............................................. A61B 17/00
[52] U.S. Cl. ............................ 128/303 R; 128/303 A
[58] Field of Search ............... 128/303 R, 303 A, 321, 128/751, 329 R

[56] References Cited

U.S. PATENT DOCUMENTS

| | | | |
|---|---|---|---|
| 3,807,409 | 4/1974 | Paparella et al. | 3/1 X |
| 3,828,791 | 8/1974 | Santos | 128/321 |
| 3,888,258 | 6/1975 | Akiyama | 128/305 |
| 3,897,786 | 8/1975 | Garnett et al. | 128/303 R |
| 3,964,468 | 6/1976 | Schulz | 128/305 X |
| 3,995,619 | 12/1976 | Glatzer | 128/303 R X |
| 4,274,414 | 6/1981 | Johnson et al. | 128/305 |

Primary Examiner—Michael H. Thaler
Attorney, Agent, or Firm—Beveridge, DeGrandi & Kline

[57] ABSTRACT

A device for inserting a myringotomy tube while permitting a twisting action to be imparted during the inserting step. A shaft of the device has a proximal and a distal end, and the proximal end is provided with a rotatable head which enables the deliberate rotation of the shaft. The distal end is adapted to releasably hold a myringotomy tube. A sleeve is provided and is adapted to movably hold a length of the shaft, while permitting the distal end of the shaft to be retracted into the sleeve. As the distal end is retracted into the sleeve, a pressure is exerted by the sleeve against a myringotomy tube held on the distal end, such that the tube is caused to be released from the distal end of the shaft. The invention also includes a provision for a handle fixedly attached to the sleeve and including a movable portion which can be caused to engage the rotatable head to move the head away from the sleeve, so that the distal end of the shaft is caused to be retracted into the sleeve.

4 Claims, 1 Drawing Figure

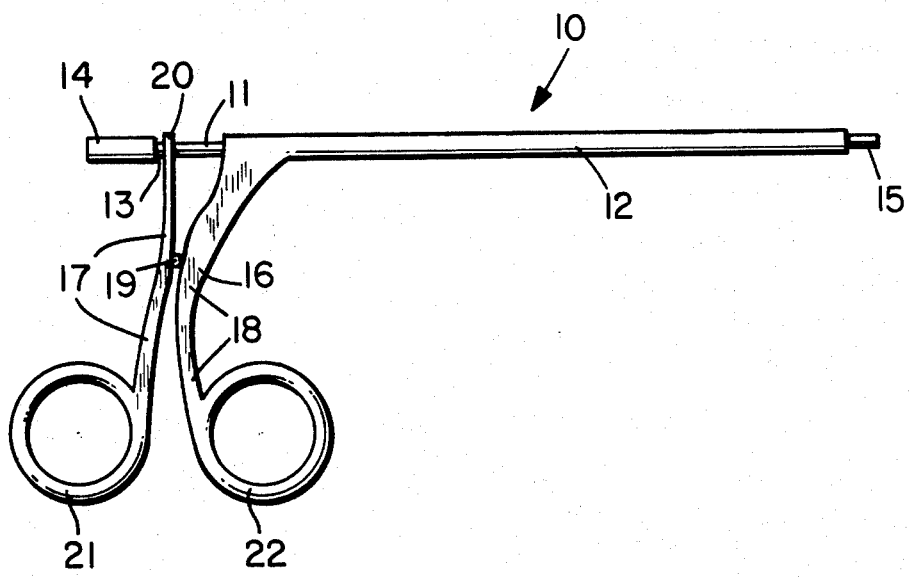

MYRINGOTOMY TUBE INSERTER AND METHOD FOR INSERTING MYRINGOTOMY TUBES

BACKGROUND OF THE INVENTION

The present invention pertains to a myringotomy tube inserter. More specifically, the present invention pertains to a myringotomy tube inserter particularly suited for use in inserting such tubes in incisions made in the tympanic membrane of the ear, including twisting of the tube to achieve full insertion.

The insertion of myringotomy drainage tubes in the tympanic membrane of the ear is a common operation which is well known in the art. The operation generally includes the steps of (1) first producing an incision in the tympanic membrane by use of a scalpel or other perforating instrument, (2) inserting a suction needle through the incision and into the middle ear to withdraw fluids therefrom, and (3) inserting a myringotomy tube into the incision.

Several means have been provided in the prior art for the insertion of myringotomy tubes in the incision of the tympanic membrane. It is not uncommon for these devices to include a shaft and a sleeve for the shaft, such that a myringotomy tube can be placed on an end of the shaft. After the tube is inserted in the incision of the ear drum, the myringotomy tube can be released from the end of the shaft by retracting the shaft into the sleeve. These devices of the prior art have met with some success for the insertion of certain types of tubes but, because no provision has been made in the prior art for the deliberate rotation of the shaft within the sleeve, the insertion devices of the prior art have met with only limited success in the insertion of other types of myringotomy tubes.

Myringotomy tubes are available in a wide variety of shapes. The essential characteristic of these tubes is that they are able to prevent the closing of the incision in the ear drum while presenting a hole through the center of the tube through which fluids can drain from the middle ear. Myringotomy tubes can be composed of many different types of materials, an example of which is a soft, pliable silicon rubber composition.

The insertion of certain types of myringotomy tubes is facilitated by a twisting action during the insertion step. As an example of such types of tubes, the description of the tube in U.S. Pat. No. 3,807,409, issued to Paparella et al is hereby incorporated by reference. The tube of U.S. Pat. No. 3,807,409 is constructed in a tubular shape having an inner and an outer flange, the inner flange being substantially larger than the outer flange. The inner flange is also characterized by a V-shaped notch which assists in the insertion of the tube. To insert the tube in the incision made in the tympanic membrane, the tube is first partly inserted into the incision and then simply twisted until the remainder of the inner flange threads itself entirely below the surface of the tympanic membrane. Myringotomy tube inserters of the prior art are unable to provide such a twisting action, since they do not provide means for the deliberate rotation of the shaft.

Thus, there exists a need in the art for a myringotomy tube inserter which enables a twisting action to facilitate the insertion of myringotomy tubes. Advantageously, the inserter will also be disposable and durable, and will allow the surgeon to observe the point of insertion without having his vision blocked by the inserting device.

SUMMARY OF THE INVENTION

A device for inserting a myringotomy tube has now been discovered which is capable of conveniently and efficiently inserting a wide variety of myringotomy tubes, including those which are inserted more easily by the application of a twisting action. The inserter of the present invention comprises a shaft which has a proximal end and a distal end, the proximal end being provided with a rotatable head which enables the deliberate rotation of the shaft, and the distal end being adapted to releasably hold a myringotomy tube. A sleeve is provided and is adapted to movably encircle a length of the shaft. By rotating the rotatable head, the myringotomy tube can be twisted to aid in its insertion. By pulling on the rotatable head, the distal end of the shaft can be retracted into the sleeve. As the distal end is retracted into the sleeve, a pressure is exerted by the sleeve against the myringotomy tube, causing the tube to be released from the distal end of the shaft. The invention also includes a provision for a handle fixedly attached to the sleeve, with the handle including a movable portion which can be caused to engage the rotatable head, pulling the head away from the sleeve, so that the distal end of the shaft is retracted into the sleeve.

BRIEF DESCRIPTION OF THE DRAWING

The drawing is a front elevational view of a preferred embodiment of a myringotomy tube inserter according to the present invention.

DESCRIPTION OF THE PREFERRED EMBODIMENTS

As can be seen in the figure, the present invention provides a novel inserter 10 for a myringotomy tube in which a twisting action can be applied during the insertion of the tube into an incision in the tympanic membrane. Inserter 10 includes a shaft 11 which is movably held along most of its length by sleeve 12. The proximal end 13 of shaft 11 is provided with a rotatable head 14 for rotating the shaft. In the quiescent position of inserter 10, the distal end 15 of shaft 11 extends from sleeve 12 and is adapted to receive and releasably hold a myringotomy tube.

Rotatable head 14 can have any of a great variety of shapes, the only requirement being that it allows the surgeon to purposefully rotate shaft 11 in order to facilitate the insertion of a myringotomy tube into an incision in the ear drum. In the embodiment depicted in the figure, rotatable head 14 consists of a knob which can be conveniently turned by the thumb and forefinger of the surgeon.

Sleeve 12 has an interior diameter which is slightly larger than the outside diameter of shaft 11, such that shaft 11 is allowed to move freely both longitudinally and rotatably within sleeve 12. Sleeve 12 is somewhat shorter than shaft 11, so that in the quiescent position of inserter 10, depicted in the figure, distal end 15 of shaft 11 extends beyond sleeve 12 to releasably hold a myringotomy tube thereon. During the use of inserter 10, sleeve 12 can be held by one hand of the surgeon while rotatable head 14 is held with the other. However, in order to facilitate the accurate positioning of the inserter, it is preferred that a handle 16 be attached to sleeve 12. Such a handle can take a wide variety of forms.

In order to release a myringotomy tube from distal end 15, shaft 11 is retracted into sleeve 12 after the tube is in position in the incision in the tympanic membrane. This retraction can be effected merely by the surgeon's rearward movement of rotatable head 14. Preferably, however, the rearward movement of rotatable head 14, to thus cause the retraction of distal end 15, is effected by the movement of a movable portion of the handle.

In the figure, a preferred handle 16 is depicted which includes means for retracting distal end 15. Handle 16 includes two substantially rigid parts 17 and 18 which are pivotably connected, at points intermediate the length of each substantially rigid part, by a pivoting section 19. Substantially rigid part 18 is fixedly attached to sleeve 12 and substantially rigid part 17 has an end 20 which encircles shaft 11 between sleeve 12 and rotatable head 14 and so is adapted to movable engage rotatable section 14 when it is desired to retract distal end 15. The free ends of substantially rigid parts 17 and 18 are preferrably provided with finger loops 21 and 22.

In the quiescent position of the inserter depicted in the figure, distal end 15 extends beyond the adjacent end of sleeve 12, so that a myringotomy tube can be placed on the distal end. When finger loops 21 and 22 are moved together, the pivoting at section 19 causes end 20 to move away from sleeve 12, moving rotatable head 14, which is engaged by end 20, away from sleeve 12 and retracting distal end 15 of shaft 11 into sleeve 12.

Inserter 10 can be composed of any suitable material which provides the necessary degree of rigidity, which can be sanitized, and which can provide for the movement of shaft 11 within sleeve 12 and for the releasable retention of a myringotomy tube on the distal end. The diameter of shaft 11 is preferably the same throughout its length and may be of a diameter up to just slightly larger than the diameter of the lumen of the myringotomy tube which is to be inserted. Rotatable head 14 can be constructed in a unitary fashion with shaft 11, or can be a separate part which is fixedly attached to shaft 11. Handle 16 can be integrally formed as a unitary construction with sleeve 12 or can be independently formed and welded or otherwise fixedly attached to the sleeve.

It will be understood that the means by which end 20 engages rotatable head 14 may be widely varied, and will depend in part upon the configuration of head 14. In the embodiment depicted in the figure, end 20 is provided with a hole which receives shaft 11 to ensure the effective engagement of rotatable head 14.

It will be readily apparent to those skilled in the art that numerous types of handles can be provided which will enable retraction of distal end 15 into sleeve 12. In a scissor-like type of handle, two substantially rigid parts can be connected and can cross each other at points intermediate their lengths, whereby their point of intersection is a hinged section. An end of one part can be fixedly attached to sleeve 11 while an end of the other part can be disposed to movably engage rotatable head 14. Because of the crossing of the substantially rigid parts in such an embodiment, distal end 15 is retracted when the free ends of the substantially rigid parts are moved away from each other.

Preferably, the inserter is disposable, so that the necessity of sanitization after use is avoided. When the myringotomy tube inserter is intended to be disposable after a single use, it is preferred to manufacture the inserter of materials which are relatively less expensive but which are durable enough to withstand the stresses of use. When it is desired to construct a myringotomy tube inserter according to the present invention which is capable of being reused for a number of operations, it is preferable to manufacture the device from sterilizable materials having greater durability.

The invention can be conveniently packaged as a kit with other instruments which are necessary in the performance of a myringotomy procedure, such as a scalpel and a suction needle, and these several components can be included in a suitably sanitized kit. It will be readily apparent to those skilled in the art that other instruments and surgical aids may likewise be included in such a kit, such as those instruments and aids described in U.S. Pat. No. 3,897,786, issued to Garnett et al.

In use, an incision is first made in the tympanic membrane of the ear by inserting a scalpel through the ear canal and incising the membrane. The scalpel is removed and, if desired, a suction needle can be used to remove any fluid from the middle ear through the incision made by the scalpel.

The novel inserter of the present invention is then used to insert a myringotomy tube into the incision in the ear drum. First, a myringotomy tube is releasably attached on the inserter by positioning the lumen of the tube onto distal end 15. Distal end 15, with the myringotomy tube in place, is then moved through the ear canal and is inserted into the incision in the tympanic membrane. Myringotomy tubes for which insertion is facilitated by a twisting action are conveniently twisted by rotation of the rotatable head 14 at an appropriate point during the insertion step. Throughout the insertion step, it is possible for the surgeon to observe the myringotomy tube and the incision, since the inserter does not obstruct the surgeon's view.

When the myringotomy tube has been successfully inserted into the incision of the ear drum, distal end 15 is then retracted into sleeve 12 by a rearward movement of shaft 11. In the preferred embodiment, depicted in FIG. 1, the rearward movement of shaft 11 is provided by the movable engagement of handle end 20 against rotatable head 14. This engagement is effected simply by moving finger holes 21 and 22 towards each other. During retraction of shaft 11, the end of sleeve 12 which is adjacent distal end 15 exerts pressure against the myringotomy tube, with the result that the myringotomy tube is caused to slide off distal end 15 as the distal end is retracted into the sleeve, and the myringotomy tube is left in the incision of the ear drum. The inserter is then removed from the ear canal and the essential steps of the myringotomy procedure are thus completed.

Although the present invention has been described in terms of preferred embodiments, it should be understood that the scope of the invention is not limited to these embodiments. Numerous modifications to the specific embodiments can be made without departing from the invention.

I claim:

1. A myringotomy tube inserter for inserting a myringotomy tube in an incision in the tympanic membrane of a patient's ear, comprising:
   an elongated hollow tubular sleeve member including
      a first handle non-rotatably attached to said sleeve member for holding and manipulating said inserter;
   a shaft member positioned within said sleeve member and having a proximal end extending from one end of said sleeve member and a distal end extending from the other end of said sleeve member, said shaft member independently movable both longitudinally and rotationally within said sleeve member, said shaft member distal end adapted to releasably hold a myringotomy tube adjacent said sleeve member other end, said shaft member proximal end terminating in an enlarged head portion adapted for gripping to enable rotation of said shaft member with respect to said sleeve member, such rotation being effective to rotate a myringotomy tube, releasably held on said distal end of said shaft member, relative to said sleeve member to permit said sleeve member and said first handle to remain in a fixed orientation as said shaft member and the myringotomy tube are rotated; and means for urging said shaft member longitudinally with respect to said sleeve member to withdraw said shaft member distal end within said sleeve member to cause said sleeve member other end to exert pressure against a myringotomy tube releasably held on said shaft member distal end, releasing the tube from said shaft member, rotation of said shaft member during insertion of the myringotomy tube into an incision in the tympanic membrane aiding such insertion, said urging means being operable upon such insertion to retract said distal end of said shaft member from the myringotomy tube.

2. The myringotomy tube inserter according to claim 1, wherein said means for urging includes a second handle slidably engaging said shaft member adjacent said enlarged head portion and movable relative to said first handle and thus to said sleeve member, such that when said second handle moves relative to said first handle, said second handle engages said enlarged head portion to move said shaft member longitudinally with respect to said sleeve member, causing said distal end of said shaft member to be retracted into said sleeve member.

3. The myringotomy tube inserter according to claim 2, wherein each of said first and second handles is provided with a finger loop.

4. A method for inserting a myringotomy tube in an ear drum, comprising the steps of making an incision in the tympanic membrane of an ear, inserting a myringotomy tube in the incision with the myringotomy tube inserter of claim 1, rotating the enlarged head portion on the shaft member of the myringotomy tube inserter to twist the myringotomy tube into the incision, and operating the urging means to withdraw the shaft member distal end within the sleeve member, releasing the myringotomy tube from the shaft member.

* * * * *